United States Patent [19]

Willard

[11] Patent Number: 5,282,784
[45] Date of Patent: Feb. 1, 1994

[54] INJECTION STENT SYSTEM

[75] Inventor: Martin R. Willard, Minneapolis, Minn.

[73] Assignee: Mentor Corporation, Minneapolis, Minn.

[21] Appl. No.: 774,068

[22] Filed: Oct. 9, 1991

[51] Int. Cl.⁵ ............................................. A61M 37/00
[52] U.S. Cl. ..................................... 604/8; 604/280
[58] Field of Search ................ 604/7, 8, 27, 264, 280, 604/281, 282, 283; 606/108

[56] References Cited

U.S. PATENT DOCUMENTS

| | | |
|---|---|---|
| 4,307,723 | 12/1981 | Finney . |
| 4,531,933 | 6/1985 | Norton et al. . |
| 4,610,657 | 9/1986 | Densow . |
| 4,627,844 | 12/1986 | Schmitt ............................ 604/264 |
| 4,643,716 | 2/1987 | Drach . |
| 4,671,795 | 6/1987 | Mulchin . |
| 4,713,049 | 12/1987 | Carter . |
| 4,787,884 | 11/1988 | Goldberg . |
| 4,790,809 | 12/1988 | Kuntz . |
| 4,790,810 | 12/1988 | Pugh, Jr. et al. . |
| 4,813,925 | 3/1989 | Anderson, Jr. et al. . |
| 4,874,360 | 10/1989 | Goldberg et al. ............ 604/281 X |
| 4,913,683 | 4/1990 | Gregory . |
| 4,931,037 | 6/1990 | Wetterman . |
| 4,950,228 | 8/1990 | Knapp, Jr. et al. . |
| 4,957,479 | 9/1990 | Roemer ................................. 604/8 |
| 4,963,129 | 10/1990 | Rusch ................................... 604/8 |
| 5,052,998 | 10/1991 | Zimmon .......................... 604/281 X |

Primary Examiner—Robert A. Hafer
Assistant Examiner—Sam Rimell
Attorney, Agent, or Firm—Hugh D. Jaeger

[57] ABSTRACT

A stent for assistance in draining urine from the kidney into the bladder through the ureter which may be partially or totally occluded. The stent has the capability to selectively inject a liquid, such as a dye, into the renal system. The stent is fabricated from a biocompatible tube, preferably of silicone rubber. The proximal and distal ends of the tube are preformed into a pigtail or other shape to secure in the renal and bladder cavities, respectively. The proximal and distal ends of the tube are perforated to provide for ingress and egress of the urine. During the implantation procedure, a guide wire is first advanced to provide a path for positioning the stent. The stent is advanced over the guide wire by pushing with a multiple diameter injection catheter. The smaller diameter proximal end of the injection catheter is positioned within the distal end of the stent at a predetermined fixed distance which occludes the distal perforations. The larger diameter distal portion of the injection catheter pushes against the distal end of the stent. Following positioning of the stent and injection of the fluid, if any, the injection catheter is released from frictional engagement with the distal end of the stent using a release catheter which slides over the injection catheter and pushes against the distal end of the stent. After removal of the injection catheter, the release catheter, and the guide wire, the stent assumes its preformed shape.

26 Claims, 4 Drawing Sheets

FIG. I

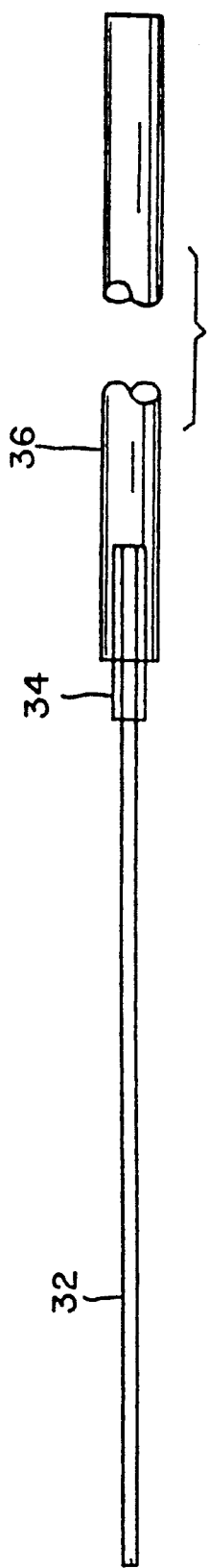

INJECTION STENT SYSTEM

BACKGROUND OF THE INVENTION

1. Field of the Invention

The present invention relates generally to implantable medical devices and more specifically relates to urinary injection stents.

2. Description of the Prior Art

It has been known for some time to treat a patient having a partially or fully occluded ureter with a stent to permit urine flow from the kidney(s) to the bladder. This occlusion may result from infection, spurious tissue growth, or inorganic deposit. An interesting, but not widely accepted, approach to the problem is found in U.S. Pat. No. 4,307,723 issued to Finney. This technique employs an essentially solid rod with external grooves for the passage of the fluid. By far the most accepted approach is to employ an implantable stent having an interior lumen for the passage of the fluid.

One of the problems addressed in the art is associated with the length of the ureter which varies from patient to patient. U.S. Pat. No. 4,790,810 issued to Pugh, Jr. et al; U.S. Pat. No. 4,643,716 issued to Drach; and U.S. Pat. No. 4,931,037 issued to Wetterman each provide a device having a stent with a length which may be adjusted by trimming at the time of manufacture or intraoperatively. U.S. Pat. No. 4,813,925 issued to Anderson, Jr. et al. suggests a stent which automatically adjusts to the length of the ureter by employing a helical shape along the body of the stent.

For most patients, the stent is implanted for a period of several weeks during which the source of the occlusion is treated. After the occlusion has been successfully abated, the stent is no longer needed and is removed from the patient. It is most desirable to remove the stent without another surgical procedure. Therefore, most present day stents employ a tether whereby the stent may be removed without more traumatic intervention. U.S. Pat. No. 4,671,795 issued to Mulchin shows a stent having the tether attached to the center of the stent rather than to the distal end. Removal of the stent using magnetic attraction is discussed in U.S. Pat. No. 4,790,809 issued to Kuntz.

To be effective, the stent must employ means for preventing migration from the implanted position. The most accepted technique is to preform the proximal and distal ends into shapes which tend to retard migration. The three most popular shapes are the helix as seen in U.S. Pat. No. 4,531,933 issued to Norton et al; the hook as shown in U.S. Pat. No. 4,874,360 issued to Goldberg et al; and the "pigtail" as employed at the proximal end of U.S. Pat. No. 4,950,228 issued to Knapp, Jr. et al. During implantation, the preformed regions are straightened through the use of a guide wire or guide catheter. Upon removal of the guiding device, the stent tends to assume its stable shape thereby preventing migration.

The implantation procedure is normally performed by advancing the stent through the urethra and the bladder into the ureter and kidney. Various early stents had an internal central lumen with a closed proximal end, such as shown in U.S. Pat. No. 4,713,049 issued to Carter. The difficulty with closed end stents is that the much smaller diameter guide wire cannot be advanced into position first but requires the initial penetration to be made with the proximal tip of the much larger diameter stent.

U.S. Pat. No. 4,610,657 issued to Densow partially addresses this difficulty by providing an open, but tapered proximal tip. This permits a small diameter guide wire to extend beyond the proximal tip of the stent whereas a larger diameter guide wire may be used to push the stent to advance it into position. This is not a complete solution, however, because it does not permit the implanting physician to advance the guide wire into position and then simply push the stent into position over it. Through the use of a complex two piece guide wire/catheter assembly, U.S. Pat. No. 4,787,884 issued to Goldberg permits the smaller diameter inner guide wire to be advanced slightly ahead of the stent. However, this technique does not permit completely advancing the guide wire before the stent enters the patient's body.

An approach which makes the implantation easier for the physician permits complete advancement of the guide wire before advancement of the stent. This is best accomplished by pushing the stent into position from its distal end using a guide catheter which slides easily over the guide wire. To accomplish this, however, it is desirable to have sufficient attachment at the distal end of the stent to transfer the necessary torque to ensure proper placement. U.S. Pat. No. 4,963,129 issued to Rusch uses a complex mechanism to interlock the proximal end of the push catheter and the distal end of the stent. Another equally complex approach is used in U.S. Pat. No. 4,957,479 issued to Roemer.

U.S. Pat. No. 4,913,683 issued to Gregory shows a stent system which is also useful for injecting a dye or other fluid. According to this design, the distal end of the stent is flared to permit engagement by the proximal tip of a pushing catheter. Unfortunately, this produces substantial strain on the distal end of the stent and therefore, restricts the types and thicknesses of material which may be used to fabricate the stent. This abutting push design also provides undesirable handling characteristics by severely limiting torque transmission from the push catheter to the stent. The Gregory design does, however, provide for the infusion of a dye or other liquid.

SUMMARY OF THE INVENTION

The present invention overcomes the disadvantages of the prior art by providing a stent system having ease of handling and implantation along with the capability of injecting a dye or other fluid through perforations in the stent. Because the stent has an open proximal end and uses a push catheter which engages the distal end of the stent, the guide wire may be completely advanced before the stent enters the patient's body. The manner in which the proximal end of the injection catheter interacts with the distal end of the stent permits optimal torque transfer and protects the stent against undue stress permitting the use of soft, biocompatible materials.

The stent is a tube of biocompatible material, such as silicone rubber, having the proximal and distal ends preformed into a known shape to prevent migration. The inside diameter and the outside diameter of the proximal tip of the stent is open and tapered to partially seal against the guide wire and to facilitate advancement. Only the proximal and distal ends are perforated to assist in controlling injection of a dye or other fluid.

A spring coil of wire, closely wound about a solid core, is used as a guide wire. It has an outside diameter sufficiently small to easily slide within the central lumen of the stent. The guide wire is freely movable with respect to the stent in both proximal and distal directions.

The injection catheter is a three piece structure having an inside diameter sufficiently large to slide freely over the guide wire. The proximal end of the injection catheter has a most proximal portion of small enough outside diameter to move within the central lumen of the stent. A length of tubing with an increased outside diameter is just distal of the most proximal portion. The proximal end of the injection catheter ensures an effective degree of torque transfer between the injection catheter and the stent; it allows advancement of the injection catheter into the stent of a predetermined distance; it provides reinforcement of the intersection of the injection catheter and the stent during advancement to protect the distal tip of the stent from deformation; and it occludes the distal perforations of the stent so that liquid infused into the stent exits only from the proximal perforations.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4 is a plan view of the injection catheter.

DETAILED DESCRIPTION OF THE PREFERRED EMBODIMENTS

Figure 1:
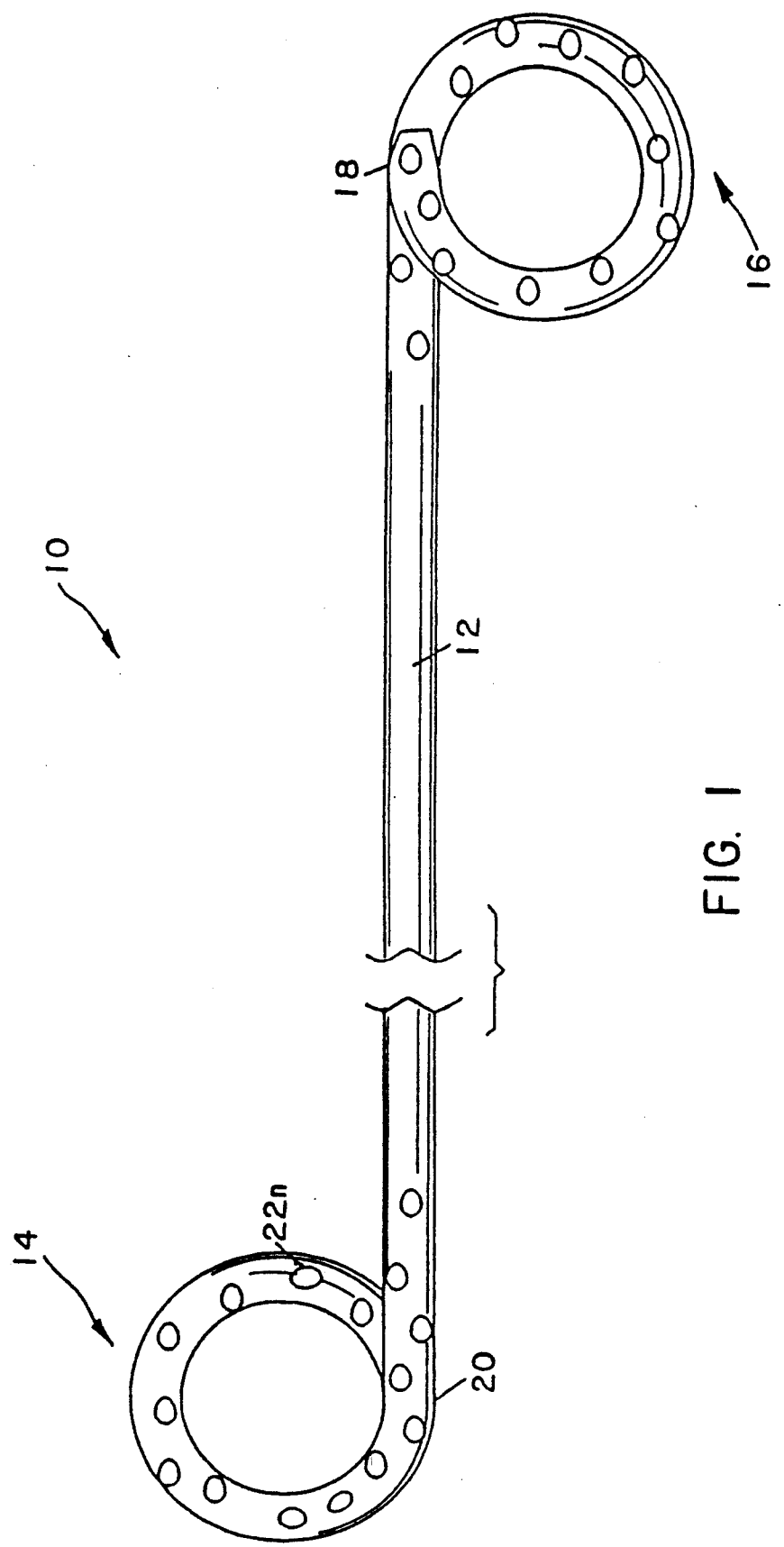
FIG. 1 is a plan view of a ureteral stent according to the present invention.

FIG. 1 is a plan view of stent 10 as shown in the stable implant position. It is fabricated from a tube of soft, biocompatible material. Silicone rubber has a number of desirable characteristics and is suitable for this purpose because of the features associated with the injection catheter as explained in more detail below.

The distal end 20 and proximal end 18 of stent 10 are open. However, proximal end 18 is tapered slightly as shown to provide a minimal seal against the guide wire (not shown in this figure) and to facilitate advancement. The distal portion and proximal portion of stent 10 contain perforations 22 (see, for example, perforation 22n). Main body 12 of stent 10 is not perforated. This provides control of the injection function as described in more detail below.

To prevent migration, the proximal portion contains preformed "pigtail" 14 to anchor securely within the renal cavity. Similarly, preformed pigtail 16 anchors firmly within the bladder. During the implant procedure, a guide wire inserted through the central lumen of stent 10 straightens preformed pigtails 14 and 16 to permit advancement to the desired implant site.

Figure 2:
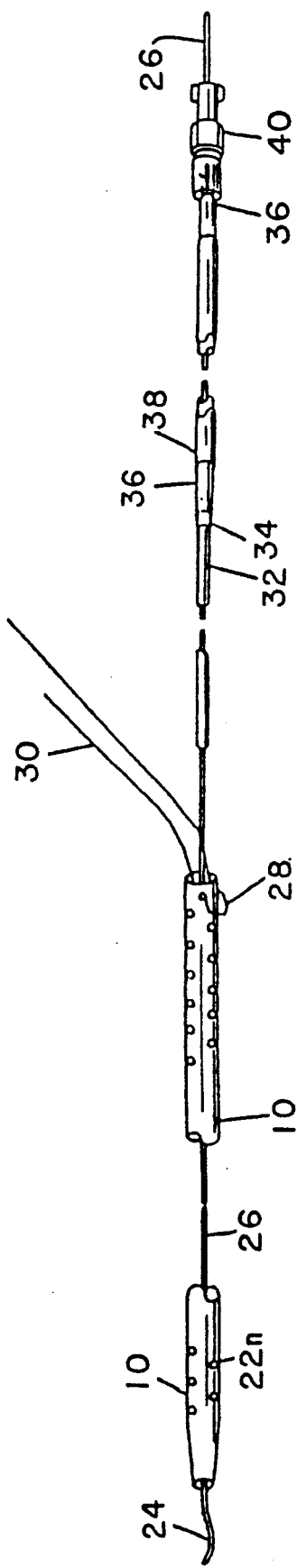
FIG. 2 is a plan view of an entire stent system.

FIG. 2 is a plan view of the components of the entire system used to implant stent 10. Preformed pigtails 14 and 16 are held straight by the relatively more stiff guide wire 26 which extends through the central lumen of stent 10. Proximal tip 24 of guide wire 26 is sufficiently floppy to steer around corners within the urinary tract. Stent 10 may be advanced along with guide wire 26 or alternatively may be pushed into position after guide wire 26 has been completely advanced.

Tether 30 consists of a piece of suture material attached to the distal end of stent 10 by loop 28. Stent 10 is removed from the patient after use by pulling on tether 30.

The injection catheter consists of three basic components. The proximal component 32 has a sufficiently large inside diameter to slide freely over guide wire 26 and a sufficiently small outside diameter to freely slide within stent 10. Proximal component 32 is chosen long enough to occlude the perforations at the distal end of stent 10 without occluding the perforations at the proximal end. This feature ensures that a dye or other fluid injected into the distal end of the injection catheter is dispensed through the proximal perforations of stent 10 but not the distal perforations. This means that the dye is injected into the kidney after stent 10 has been properly positioned.

Intermediate portion 34 is a relatively short piece of tubing fixedly attached to proximal component 32. The inside diameter of intermediate portion 34 is sufficient to permit proximal component 32 to be snugly fitted therein. Preferably, the intersection of proximal component 32 and intermediate portion 34 are adhesively coupled. The outside diameter of intermediate portion 34 is sufficiently large to fit snugly within stent 10. This snug fit provides frictional engagement of the injection catheter with stent 10 and serves to reinforce stent 10 as it is being advanced.

Distal portion 36 of the injection catheter is a relatively long piece of flexible tubing of a convenient polymer. The inside diameter of distal portion 36 snugly accepts intermediate portion 34. Distal portion 36 and intermediate portion 34 are fixedly joined, preferably by adhesive means. The outside diameter of distal portion 36 is large enough to ensure that the proximal tip of distal portion 36 abuts the distal tip of stent 10. In this way, force on distal portion 36 of the injection catheter advances stent 10. If the distal end of guide wire 26 is held stationary, this advancement is with respect to guide wire 26.

Touhy-borst connector 40 provides a standardized means to seal the distal end of the assembly and provides an access port for the entry of a pressurized fluid for dispensing via the proximal perforations of stent 10. Release catheter 38 has a large enough inside diameter to slide freely over distal portion 36 of the injection catheter. It must also abut the distal tip of stent 10. After placement of stent 10 and injection of the required fluid, release catheter 38 is advanced to hold the distal end of stent 10 in place while the injection catheter is removed. This is necessary because intermediate portion 34 fits snugly enough to frictionally engage the distal end of stent 10.

Figure 3:
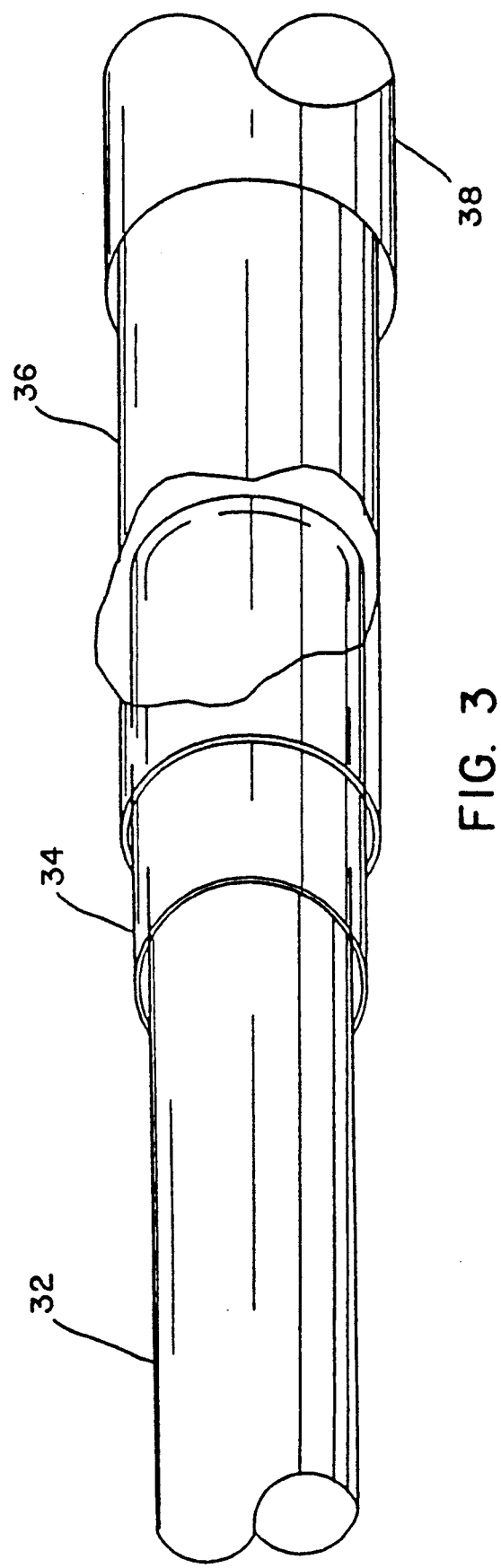
FIG. 3 is a close up perspective view of the three portions of the injection catheter.

FIG. 3 is a close up perspective view of the three components of the injection catheter. In the preferred embodiment and not to be considered as limiting of the present invention, proximal component 32 is adhesively attached to intermediate portion 34 which is in turn adhesively attached to distal portion 36. All other referenced components are as previously described.

FIG. 4 is a plan view of the injection catheter. Preferably, and not to be considered as limiting, proximal component 32, intermediate portion 34, and distal portion 36 are fabricated from polyurethane, polyethylene, or other suitable tubing of the appropriate dimensions.

Having thus described the preferred embodiments of the present invention, those of skill in the art will be readily able to apply the teachings found herein to yet other embodiments within the scope of the claims hereto attached.

I claim:

1. A stent system comprising:
   a. a stent of biocompatible material having a central lumen and having a proximal end and a distal end;
   b. a guide wire moveable within said central lumen of said stent;
   c. means moveable over said guide wire for pushing said stent over said guide wire; and
   d. means coupled to said pushing means for reinforcing said stent when said pushing means pushes said stent over said guide wire
   said means coupled to said pushing means being moveable within said stent for occluding said perforations at said distal end.

2. A stent system according to claim 1 wherein said stent has perforations at said proximal end and said distal end.

3. A stent system according to claim 1 further comprising means moveable over said pushing means for releasing said reinforcing means from engagement with said stent.

4. A stent system according to claim 3 wherein said reinforcing means limits the travel of said occluding means to a predetermined position within said stent.

5. A stent system according to claim 4 further comprising a tether fixedly attached to said stent.

6. A stent system according to claim 5 wherein said proximal end and said distal end of said stent are preformed to prevent migration.

7. A stent system according to claim 6 wherein said preforming is in the form of a pigtail.

8. A stent system according to claim 7 wherein said pushing means further comprises means for injecting a fluid.

9. A stent system according to claim 8 wherein said injecting means has a distal end including a touhy-borst connector.

10. The stent system according to claim 1 wherein:
    c. said pushing means as movable over said guide wire for pushing said stent into position having a proximal end with a plurality of diameters for frictional engagement within said stent.

11. A ureteral stent system comprising:
    a. a stent made from a soft compliant single lumen tube with perforated proximal and distal ends having preformed retention means on said proximal and distal ends and having a relatively straight unperforated central portion intermediate said proximal and distal ends; and
    b. an infusion catheter having proximal and distal ends and having a plurality of diameters at said proximal end for frictional engagement with said distal end of said stent.

12. A ureteral stent system according to claim 11 wherein said infusion catheter occludes said perforations of said distal end of said stent when said infusion catheter is frictionally engaged within said distal end of said stent.

13. A ureteral stent system according to claim 10, 11 or 12 wherein said stent is made of silicone rubber.

14. A ureteral stent system according to claim 13 wherein said infusion catheter reinforces said distal end of said stent when said proximal end of said infusion catheter is frictionally engaged within said distal end of said stent.

15. A ureteral stent system according to claim 10, 11, or 12 wherein said infusion catheter reinforces said distal end of said stent when said proximal end of said infusion catheter is frictionally engaged within said distal end of said stent.

16. An indwelling ureteral stent system comprising:
    a. an elongated relatively flexible hollow tubular member having two preformed end portions and perforations through said stent in the vicinity of said end portions and having a relatively straight unperforated central portion intermediate said two preformed end portions; and
    b. an infusion catheter means comprising a multi-diameter end portion for frictional engagement of a one of said end portions and for occluding said perforations in the vicinity of said one of said end portions.

17. An indwelling ureteral stent system according to claim 16 wherein said multi-diameter end portion of said infusion catheter means has three diameters.

18. An indwelling ureteral stent system according to claim 16 or 17 wherein said infusion catheter means further comprises an adapter for infusing fluids through said infusion catheter means and said stent.

19. An indwelling ureteral stent system according to claim 18 wherein said infusion catheter means further comprises means for reinforcing said one of said two end portions of said stent.

20. A stent system comprising:
    a. a stent of biocompatible material having a central lumen and having a proximal end and a distal end, and including perforations at said proximal end and said distal end;
    b. a guide wire moveable within said central lumen of said stent;
    c. means moveable over said guide wire for pushing said stent over said guide wire;
    means coupled to said pushing means for reinforcing said stent when said pushing means pushes said stent over said guide wire; and,
    e. said pushing means moveable within said stent for occluding said perforations at said distal end
    and further comprising means movable over said pushing means for releasing said reinforcing means from engagement with said stent.

21. A stent system according to claim 20 wherein said reinforcing means limits the travel of said occluding means to a predetermined position within said stent.

22. A stent system according to claim 21 further comprising a tether fixedly attached to said stent.

23. A stent system according to claim 22 wherein said proximal end and said distal end of said stent are preformed to prevent migration.

24. A stent system according to claim 23 wherein said preforming is in the form of a pigtail.

25. A stent system according to claim 24 wherein said pushing means further comprises means for injecting a fluid.

26. A stent system according to claim 25 wherein said injecting means has a distal end including a connector.

* * * * *